United States Patent
Bodkhe et al.

(10) Patent No.: US 12,295,923 B2
(45) Date of Patent: May 13, 2025

(54) ANTIMICROBIAL COMPOSITIONS WITH 1,2-ALKANEDIOLS

(71) Applicant: Solventum Intellectual Properties Company, Maplewood, MN (US)

(72) Inventors: Rajan B. Bodkhe, Woodbury, MN (US); Ranjani V. Parthasarathy, Woodbury, MN (US); Matthew T. Scholz, Woodbury, MN (US); Naimul Karim, Maplewood, MN (US); Petra L. Kohler Riedi, Minneapolis, MN (US); Joseph J. Stoffel, Hastings, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 958 days.

(21) Appl. No.: 17/418,718

(22) PCT Filed: Dec. 23, 2019

(86) PCT No.: PCT/IB2019/061284
§ 371 (c)(1),
(2) Date: Jun. 25, 2021

(87) PCT Pub. No.: WO2020/136552
PCT Pub. Date: Jul. 2, 2020

(65) Prior Publication Data
US 2022/0079893 A1     Mar. 17, 2022

Related U.S. Application Data

(60) Provisional application No. 62/785,365, filed on Dec. 27, 2018.

(51) Int. Cl.
| | |
|---|---|
| *A61K 31/14* | (2006.01) |
| *A01N 31/02* | (2006.01) |
| *A01N 37/06* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/32* | (2006.01) |
| *A61P 31/02* | (2006.01) |
| *A01N 33/04* | (2006.01) |
| *A01N 37/04* | (2006.01) |

(52) U.S. Cl.
CPC .............. *A61K 31/14* (2013.01); *A61K 47/10* (2013.01); *A61K 47/12* (2013.01); *A61K 47/14* (2013.01); *A61K 47/183* (2013.01); *A61K 47/32* (2013.01); *A61P 31/02* (2018.01)

(58) Field of Classification Search
CPC ........ A61K 31/14; A61K 47/10; A61K 47/12; A61K 47/14; A61K 47/183; A61K 47/32; A61P 31/02; A01N 31/02; A01N 37/04; A01N 37/06; A01N 33/04
See application file for complete search history.

(56) References Cited

U.S. PATENT DOCUMENTS

| | | |
|---|---|---|
| 3,930,000 A | 12/1975 | Margraf |
| 4,206,215 A | 6/1980 | Bailey |
| 4,420,484 A | 12/1983 | Gorman |
| 4,442,125 A | 4/1984 | Thiele |
| 5,665,776 A | 9/1997 | Yu |
| 6,238,682 B1 | 5/2001 | Klofta |
| 6,700,032 B1 | 3/2004 | Gray |
| 6,998,509 B1 | 2/2006 | Nielsen |
| 8,512,723 B2 | 8/2013 | Scholz |
| 8,940,324 B2 | 1/2015 | Aydinoglu |
| 9,486,420 B1 | 11/2016 | Myntti |
| 10,016,501 B2 | 7/2018 | Scholz |
| 2001/0003693 A1 | 6/2001 | Gessner |
| 2005/0035327 A1 | 2/2005 | Canada |
| 2006/0210613 A1 | 9/2006 | Carliss |
| 2009/0069436 A1 | 3/2009 | MacGregor |
| 2009/0076084 A1 | 3/2009 | Krug |

(Continued)

FOREIGN PATENT DOCUMENTS

| | | |
|---|---|---|
| AU | 2017204534 | 7/2017 |
| CA | 2992543 | 4/2017 |

(Continued)

OTHER PUBLICATIONS

DailyMed, Salicylic Acid 3% Topical Ointment product insert, 2018 (Year: 2018).*
Block, Disinfection, Sterilization, and Preservation, 912-932 (1968).
Kiser, "Development and Characterization of a *Staphylococcus aureus* Nasal Colonization Model in Mice", Infect and Immunity, Oct. 1999, vol. 67, No. 10, pp. 5001-5006.
Kramer, "Influence of the Antiseptic Agents Polyhexanide and Octenidine on FL Cells and on Healing of Experimental Superficial Aseptic Wounds in Piglets", Skin Pharmacology and Physiology, 2004, vol. 17, No. 3, pp. 141-146.
Nicoletti, "The Antimicrobial Activity in vitro of chlorhexidine, a mixture of isothiazolinones ('Kathon' CG) and cetyl trimethyl ammonium bromide (CTAB)", Journal of Hospital Infection, 1993, vol. 23, pp. 87-111.

(Continued)

*Primary Examiner* — Jeffrey H Murray
*Assistant Examiner* — Kevin S Martin

(57) ABSTRACT

Compositions including a quaternary amine antiseptic component having a concentration of at least about 0.04% by weight; a poly carboxylic acid chelator having a concentration of at least about 0.05 M and/or an alphahydroxy acid buffer having a concentration of at least about 0.05 M; a (C8-C12) 1,2 alkane diol; and optionally water are provided. The compositions have a pH greater than or equal to 3.5 and less than 5.5 at 23° C. In certain embodiments, water is present in the composition at a greater weight percent than each of the quaternary amine antiseptic component; the polycarboxylic acid chelator, if present; the alphahydroxy acid buffer, if present; and the (C8-C12) 1,2-alkane diol. In certain embodiments, water is present in the composition at a greater weight percent than any other component.

15 Claims, No Drawings

(56) References Cited

U.S. PATENT DOCUMENTS

| | | |
|---|---|---|
| 2010/0282409 A1 | 11/2010 | Hobbs |
| 2012/0070510 A1 | 3/2012 | Krug |
| 2012/0107415 A1 | 5/2012 | Lisowsky |
| 2012/0201902 A1 | 8/2012 | Modak |
| 2013/0150451 A1 | 6/2013 | Salamone |
| 2014/0044667 A1 | 2/2014 | Greff |
| 2015/0189872 A1 | 7/2015 | Gradtke |
| 2016/0073628 A1 | 3/2016 | Myntti |
| 2016/0374352 A1 | 12/2016 | Modak |
| 2017/0273305 A1 | 9/2017 | Kohler Riedi |
| 2017/0290789 A1 | 10/2017 | Dicosmo |

FOREIGN PATENT DOCUMENTS

| | | |
|---|---|---|
| CN | 107982094 A | 5/2018 |
| DE | 3925540 | 8/1990 |
| EP | 1139759 | 10/2001 |
| EP | 1404311 | 4/2004 |
| EP | 1638417 | 3/2006 |
| EP | 1683416 | 7/2006 |
| EP | 2896395 | 7/2015 |
| WO | WO1993-00100 | 1/1993 |
| WO | WO2001-66084 | 9/2001 |
| WO | WO2005-058381 | 6/2005 |
| WO | WO2006-039961 | 4/2006 |
| WO | WO2007-031519 | 3/2007 |
| WO | WO2007-068938 | 6/2007 |
| WO | WO2013-086181 | 6/2013 |
| WO | WO2016-156869 | 10/2016 |

OTHER PUBLICATIONS

Nussbaum, "An Economic Evaluation of the Impact, Cost, and Medicare Policy Implications of Chronic Nonhealing Wounds", Value in Health, Jan. 2018, vol. 21, No. 1, pp. 27-32.

Sciarra, "Aerosols", Remington's Pharmaceutical Sciences, 1990, pp. 1694-1712.

Starek, "Hematological effects of four ethylene glycol monoalkyl ethers in short-term repeated exposure in rats", Archives of Toxicology, 2008, vol. 82, No. 2, pp. 125-136.

Vorum, "Solubility of Long-Chain Fatty Acids in Phosphate Buffer at pH 7.4", Biochimica et. Biophysica Acta, 1992, vol. 1126, pp. 135-142.

International Search Report for PCT International Application No. PCT/IB2019/061284, mailed on Mar. 19, 2020, 4 pages.

* cited by examiner

ANTIMICROBIAL COMPOSITIONS WITH 1,2-ALKANEDIOLS

CROSS REFERENCE TO RELATED APPLICATIONS

This application is a national stage filing under 35 U.S.C. 371 of PCT/IB2019/061284 filed 23 Dec. 2019, which claims the benefit of U.S. Provisional Application No. 62/785,365, filed 27 Dec. 2018, the disclosures of each of which are incorporated by reference herein in their entireties.

BACKGROUND

The use of antimicrobial agents plays an important part in current medical therapy. This is particularly true in the fields of dermatology as well as skin and wound antisepsis, where the most effective course of treatment for skin, mucous membranes, or open wounds, which are afflicted with bacterial, fungal, or viral infections or lesions, frequently includes the use of a topical antimicrobial agent, such as antibiotics. For decades medicine has relied primarily upon antibiotics to fight systemic as well as topical infections.

Antibiotics are organic molecules produced by microorganisms that have the capacity in dilute solutions (e.g., solutions less than 10 µg/ml and often less than 1 µg/ml) to destroy or inhibit the growth of bacteria and other microorganisms. They are generally effective at very low levels and are often safe with very few, if any, side effects. Antibiotics are commonly of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means. Not only does resistance eliminate the ability of a medication to treat an affliction, but it can also put the patient at further risk, especially if the antibiotic is one that is routinely used systemically.

Antiseptics, on the other hand, are synthetic molecules that destroy or inhibit microorganisms and virus by inhibiting metabolic pathways or altering the cell envelope or both. They tend to have broader spectrum of antimicrobial activity and often act by nonspecific means such as disruption of cell membranes, oxidation of cellular components, denaturation of proteins, etc. This nonspecific activity makes it difficult for microorganisms to develop clinical resistance to antiseptics. For example, there are very few reports of clinical resistance to antiseptics such as iodine, lower alcohols (ethanol, propanol, etc.), chlorhexidine, quaternary amine surfactants, chlorinated phenols, and the like. Some of these compounds, however, need to be used at concentrations that often result in irritation or tissue damage, especially if applied repeatedly. Furthermore, unlike antibiotics, many antiseptics are not active in the presence of high levels of organic compounds. For example, formulations containing iodine or quaternary ammonium compounds have been reported to be inactivated by the presence of organic matter such as that in nasal or vaginal secretions, and perhaps even on skin.

The formulation of components can affect the performance and potential irritation of antimicrobial agents. For example, many conventional antimicrobial compositions are too low in viscosity and/or too hydrophilic in nature to maintain sufficient substantivity and persistence to provide sufficient antimicrobial activity on moist tissue, such as the anterior nares or open, exuding, or infected lesions. It has been reported that the presence of solvents can diminish the antimicrobial activity of many antiseptics. Furthermore, it has been reported that many surfactants can reduce the efficacy of antiseptics by sequestering the antiseptic in micelles. (H. B. Kostenbauer, Chapter 44 in "Disinfection, Sterilization, and Preservation", First addition, 1968, C. A. Lawrence and S. S. Block). Additionally, surfactants are often implicated in contributing to irritation.

Thus, there is still a need for effective antimicrobial compositions that develop little resistance and are well-tolerated when used on mammalian tissue and especially on moist mammalian tissue such as in the nasal passages, anterior nares, vagina, and wounds.

SUMMARY

The present disclosure provides antimicrobial compositions and methods of using the compositions. Such compositions are typically useful when applied topically, particularly to mucosal tissues (i.e., mucous membranes), although a wide variety of surfaces can be treated. They can provide effective reduction, prevention, or elimination of microbes, particularly bacteria, fungi, and viruses. Preferably, the microbes are of a relatively wide variety such that the compositions of the present invention have a broad spectrum of activity.

Advantageously, compositions of the present invention provide effective topical antimicrobial activity and are accordingly useful in the local treatment and/or prevention of conditions that are caused, or aggravated by, microorganisms (including viruses, bacteria, fungi, *mycoplasma*, and protozoa) on skin, wounds, and/or mucous membranes.

In one aspect, a composition of the present disclosure can comprise a quaternary amine antiseptic component having a concentration of at least about 0.04% by weight; a polycarboxylic acid chelator having a concentration of at least about 0.05 M and/or an alphahydroxy acid buffer having a concentration of at least about 0.05 M; a (C8-C12) 1,2 alkane diol; and water. The composition can have a pH that is greater than or equal to 3.5 and less than 5.5 at 23° C. The water is present in the composition at a greater weight percent than each of the quaternary amine antiseptic component; the polycarboxylic acid chelator, if present; the alphahydroxy acid buffer, if present; and the (C8-C12) 1,2-alkane diol. In certain embodiments the water is present in greatest amount.

In another aspect, a composition of the present disclosure can comprise a quaternary amine antiseptic component having a concentration of at least about 0.04% by weight; a polycarboxylic acid chelator having a concentration of at least about 0.05 M and/or an alphahydroxy acid buffer having a concentration of at least about 0.05 M; a (C8-C12) 1,2 alkane diol; and, optionally, water. The water can be present in these compositions from 0% to about 75% by weight. When the composition comprises ≥50% water by weight, the composition has a pH that is greater than or equal to 3.5 and less than 5.5 at 23° C. When the composition comprises <50% water by weight, a diluted composition, made by diluting the composition 1:1 (w/w) with deionized water and thoroughly mixing, has a pH that is greater than or equal to 3.5 and less than 5.5 at 23° C.

In another aspect, a composition of the present disclosure can comprise an antiseptic component comprising at least 2 quaternary ammonium groups per molecule and having a concentration of at least about 0.04% by weight; a polycarboxylic acid chelator having a concentration of at least about 0.05 M and/or an alphahydroxy acid buffer having a concentration of at least about 0.05 M; a (C8-C12) 1,2 alkane diol; and, optionally, water.

In yet another aspect, a composition of the present disclosure can comprise a quaternary amine antiseptic component having a concentration of at least about 0.04% by weight; a polycarboxylic acid chelator having a concentration of at least about 0.05 M and/or an alphahydroxy acid buffer having a concentration of at least about 0.05 M; a (C8-C12) 1,2 alkane diol; and water. The composition can have a pH that is greater than or equal to 3.5 and less than 5.5 at 23° C. The water is present in the composition at a greater weight percent than any other component of the composition.

In any of the above embodiments, the quaternary amine antiseptic component can be selected from the group consisting of, a benzethonium salt, a C12-C18 alkylpyridinium salt, C12-C18 alkyltrimethylammonium salt, a di-(C8-C16) alkyldimethyl ammonium salt, a polyquaternary amine salt compound, an alkyldimethylbenzylammonium salt, or an octenidine salt may be used and a combination of any two or more of the foregoing quaternary amine and octenidine antiseptic components.

In any of the above embodiments, the polycarboxylic acid chelator can be selected from the group consisting of citric acid or a salt thereof, succinic acid or a salt thereof, malic acid or a salt thereof, tartaric acid or a salt thereof, adipic acid or a salt thereof, ethylenediamine-N,N,N',N'-tetraacetic acid or a salt thereof, and ethylene glycol-bis(b-aminoethyl ether)-N,N,N',N'-tetraacetic acid or a salt thereof, ethylenediamine-N,N'-bis(2-hydroxyphenylacece acid), polyphosphate salts, polyphosphonic acid salts and combinations thereof.

In any of the above embodiments, the composition further can comprise a betahydroxy acid. The betahydroxy acid can be selected from the group consisting of betahydroxypropionic acid, salicylic acid, betahydroxybutanoic acid, tropic acid, and trethocanic acid.

In any of the above embodiments, the (C8-C12) 1,2 alkane diol can comprise 1,2-octane diol.

In yet another aspect, the present disclosure provides a method of treating a wound. The method can comprise applying the composition of any one of the above embodiments to a wound site.

Importantly, the compositions of the present invention are capable of destroying microorganisms on or in mammalian tissue. Therefore, the concentrations employed are generally greater than those that have been used to simply preserve certain topically applied compositions, i.e., prevent the growth of microorganism in topical compositions for purposes other than antisepsis. For example, the concentration may be at least 0.1 wt %, preferably at least 0.2 wt % and more preferably at least 0.5 wt %. Commonly, the antiseptics may be employed at concentration of at least 1 wt-%, preferably at least 2 wt-% and often at least 3% by weight of the composition. All weight percentages are based on the total weight of a "ready to use" or "as used" composition.

"Effective amount", as used herein, means the amount of the one or more antiseptic components when in a composition, as a whole, provides antimicrobial (including, for example, antiviral, antibacterial, or antifungal) activity that when applied in an amount, at a frequency, and for a duration, reduces, prevents, or eliminates one or more species of microbes such that an acceptable level of the microbe results. Typically, this is a level low enough not to cause clinical symptoms and is desirably a non-detectable level. It should be understood that in the compositions of the present invention, the concentrations or amounts of the components, when considered separately, may not kill to an acceptable level, or may not kill as broad a spectrum of undesired microorganisms, or may not kill as fast; however, when used together such components provide an enhanced antimicrobial activity (as compared to the same components used alone under the same conditions). Also, it should be understood that (unless otherwise specified) the listed concentrations of the components are for "ready to use" or "as used" compositions. The compositions can be in a concentrated form. That is, certain embodiments of the compositions can be in the form of concentrates that would be diluted by the user with an appropriate vehicle.

"Hydrophilic" or "water-soluble" refers to a material that will disperse or dissolve in deionized water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and mixing the composition thoroughly it appears uniform clear solution without visible cloudiness, phase separation, or precipitate in a jar having a path length of 4 cm. Typically when placed in 1×1 cm cell, the samples exhibit greater than 70% transmission measured in a suitable spectrophotometer at a wavelength of 655 nm. Water dispersible hydrophilic materials disperse in water to form uniform cloudy dispersions after vigorous shaking of a 5% by weight mixture of the hydrophilic component in water. Preferred hydrophilic components are water-soluble.

"Hydrophobic" or "water-insoluble" refers to a material that will not significantly dissolve in deionized water at 23° C. "Not significantly" means that the solubility in water of the material is less than 5% by weight, preferably less than 1% by weight, more preferably less than 0.5% by weight, and even more preferably less than 0.10% by weight, based on the total weight of the hydrophobic material and the water. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4 cm path length the sample should have evidence of a second phase which can be liquid or solid and may be separated on the top, bottom, or distributed throughout the sample. For crystalline compounds care must be taken to avoid producing a supersaturated solution. The components should be mixed and observed. Cloudiness or presence of a visible precipitate or separate phase indicates that the solubility limit has been exceeded. Typically, when placed in 1×1 cm cell the sample has less than 70% transmission measured in a suitable spectrophotometer at a wavelength of 655 nm. For solubility determinations less than that which can be observed with the naked eye, the solubility is determined using radiolabeled compounds as described under "Conventional Solubility Estimations" in *Solubility of Long-Chain Fatty Acids in Phosphate Buffer at pH 7.4*, Henrik Vorum, et. al., *Biochimica et. Biophysica Acta.* 1126 (1992) 135-142, which is incorporated herein by reference in its entirety.

"Antibiotic" means an organic chemical compound produced by microorganisms that has the ability in dilute concentrations (e.g. <3% wt/wt) to destroy or inhibit microorganisms and is used to treat infectious disease. This may also encompass semi-synthetic compounds that are chemical derivatives of the compound produced by microorganisms or synthetic compounds that act on very specific biochemical pathways necessary for the cell's survival.

"Antiseptic" means a chemical agent described herein that kills pathogenic and non-pathogenic microorganisms. Preferred antiseptics exhibit at least 4 log reduction of both *P. aeruginosa* and *S. aureus* in 60 minutes from an initial inoculum of $1-3 \times 10^7$ cfu/ml when tested in Mueller Hinton broth at 35° C. at a concentration of 0.25 wt % in a Rate of Kill assay using an appropriate neutralizer as described in *The Antimicrobial Activity in vitro of chlorhexidine, a mixture of isothiazolinones (Kathon CG) and cetyl trimethyl ammonium bromide (CTAB)*, G. Nicoletti, V. Boghossian, F. Gurevitch, R. Borland and P. Mogenroth, *Journal of Hospital Infection*, (1993), vol. 23, pp 87-111, which is incorporated herein by reference in its entirety. Antiseptics generally interfere more broadly with the cellular metabolism and/or the cell envelope. Antiseptics may be small molecule or polymeric. Small molecule antiseptics generally have molecular weights less than about 500 and preferably less than 350 g/mole. Polymeric antiseptics can be much higher in molecular weight.

"Preservative" as used herein refers to antiseptics which are incorporated into a composition to prevent biological contamination and/or deterioration of a composition. These are generally present at levels of less than 0.50 by weight and often less than about 0.1% by weight.

"Decolonization" refers to a reduction in the number of microorganisms (e.g., bacteria and fungi) present in or on tissue that do not necessarily cause immediate clinical symptoms. Examples of decolonization include, but are not limited to, decolonization of the nasal cavity and wounds. Ordinarily fewer microorganisms are present in "colonized tissue" than in "infected tissue." When the tissue is completely decolonized the microorganisms have been "eradicated".

"Subject" and "patient" includes humans, sheep, horses, cattle, pigs, dogs, cats, rats, mice, or other mammals.

"Wound" refers to an injury to a subject which involves a break in the normal skin or mucosal tissue barrier exposing tissue below, which is caused by, for example, lacerations, surgery, burns, damage to underlying tissue such as pressure sores, poor circulation, and the like. Wounds are understood to include both acute and chronic wounds.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

The present invention provides antimicrobial (including, e.g., antiviral, antibacterial, and antifungal) compositions. These compositions include one or more antimicrobial (C8-C12) 1,2-alkane diol. The compositions also include a quaternary amine antiseptic component having a concentration of at least about 0.04% by weight. In addition, the compositions include a polycarboxylic acid chelator of at least about 0.05 M. Certain compositions include an alphahydroxy acid buffer component having a concentration of at least about 0.05 M instead of or in addition to the polycarboxylic acid chelator. In certain preferred embodiments the alphahydroxyacid also is a polycarboxylic acid such as citric, malic, and tartaric acids. A composition of the present disclosure has a pH that is greater than or equal to 3.5 and less than 5.5 at 23° C.

A composition of the present disclosure optionally comprises water. In certain embodiments, the water is present in the composition at a greater weight percent than each of the quaternary amine antiseptic component; the polycarboxylic acid chelator, if present; the alphahydroxy acid buffer, if present; and the (C8-C12) 1,2-alkane diol. In certain embodiments, the water is present in the composition at a greater weight percent than any other component of the composition.

In certain embodiments, the water is present in the composition from 0% to about 75% by weight. When the composition comprises ≥50% water by weight, the composition has a pH that is greater than or equal to 3.5 and less than 5.5 at 23° C. When the composition comprises <50% water by weight, a diluted composition, made by diluting the composition 1:1 (w/w) with deionized water and thoroughly mixing, has a pH that is greater than or equal to 3.5 and less than 5.5 at 23° C.

Such compositions adhere well to bodily tissues (i.e., mammalian tissues such as skin, mucosal tissue, and wounds) and thus are very effective topically. Thus, the present invention provides a wide variety of uses of the compositions. Particularly preferred methods involve topical application, particularly to skin lesions, wounds, and mucosal tissues (i.e., mucous membranes including the anterior nares and other tissues of the upper respiratory tract). Herein, such tissues are preferred examples of mammalian tissues.

Compositions of the present invention can be used to provide effective topical antimicrobial activity. For example, they can be used for hand disinfection, particularly in presurgical hand antisepsis. They can be used to disinfect various body parts, particularly in patient presurgical skin antiseptics.

Compositions of the present invention can be used to provide effective topical antimicrobial activity and thereby treat and/or prevent a wide variety of afflictions. For example, they can be used in the treatment and/or prevention of afflictions that are caused, or aggravated by, microorganisms (e.g., Gram positive bacteria, Gram negative bacteria, fungi, protozoa, *mycoplasma*, yeast, viruses, and even lipid-enveloped viruses) on skin and/or mucous membranes, such as those in the nose (anterior nares, nasopharangyl cavity, nasal cavities, etc.), outer ear, and middle ear, mouth, rectum, vagina, or other similar tissues. Particularly relevant organisms that cause or aggravate such afflictions include *Staphylococcus* spp., *Streptococcus* spp., *Pseudomonas* spp., *Enterococcus* spp., and *Escherichia* spp., bacteria, as well as herpes virus, *Aspergillus* spp., *Fusarium* spp. *Candida* spp. as well as combinations thereof. Particularly virulent organisms include *Staphylococcus aureus* (including resistant strains such as Methicillin Resistant *Staphylococcus Aureus* (MRSA), *Staphylococcus epidermidis, Streptococcus pneumoniae, Enterococcus faecalis*, Vancomycin Resistant *Enterococcus* (VRE), *Pseudomonas aeruginosa, Escherichia coli, Aspergillus niger, Aspergillus fumigatus, Aspergillus clavatus, Fusarium solani, Fusarium oxysporum, Fusarium chlamydosporum, Candida albicans, Candida glabrata, Candida krusei*, and combinations thereof.

Compositions of the present invention can be used for the prevention and/or treatment of one or more microorganism-caused infections or other afflictions. In particular, compositions of the present invention can be used for preventing and/or treating one or more of the following: skin lesions, conditions of the skin such as impetigo, eczema, diaper rash in infants as well as incontinent adults, inflammation around ostomy devices, shingles, and bacterial infections in open wounds (e.g., cuts, scrapes, burns, lacerations, chronic wounds); necrotizing faciitis; infections of the outer ear; acute or chronic otitis media (middle ear infection) caused by bacterial, viral, or fungal contamination; fungal and bacterial infections of the vagina or rectum; vaginal yeast infections; bacterial rhinitis; ocular infections; cold sores; genital herpes; colonization by *Staphylococcus aureus*, in the anterior nares (e.g., prior to surgery or hemodialysis); mucositis (inflammation of a mucous membrane typically induced by non-invasive fungi); chronic sinusitis (e.g., that caused by bacterial or viral contamination); non-invasive fungus-induced rhinosinusitis; chronic colitis; Crohn's disease; burns; napkin rash; tinea pedis (i.e., athlete's foot); tinea curis (i.e., jock itch); tinea corporis (i.e., ringworm); candidiasis; strep throat, strep pharyngitis, and other Group A Streptococci infections; rosacea (often called adult acne); psoriasis; common cold; and respiratory afflictions (e.g., asthma).

In sum, compositions of the present invention can be used for preventing and/or treating a wide variety of topical afflictions caused by microbial infection (e.g., yeast, viral, bacterial infections).

Compositions of the present invention can be used on a wide variety of surfaces. For example, they can be used on mammalian tissues (particularly, skin, mucosal tissue, chronic wounds, acute wounds, burns, and the like) and hard surfaces such as medical (e.g., surgical) devices, floor tiles, countertops, tubs, dishes, as well as on gloves (e.g., surgical gloves). They can also be delivered from swabs, cloth, sponges, foams, nonwovens, and paper products (e.g., paper towels and wipes), for example. Typically, compositions with hydrophobic components are used on mammalian tissues (particularly, skin, mucosal tissue, wounds) and medical devices that come in contact with such surfaces, whereas compositions with hydrophilic components are used on these surfaces as well as other hard surfaces (e.g., floor tiles).

Thus, the present invention also provides various methods of use of compositions of the present invention. Various embodiments of the present invention include: a method of preventing an affliction caused, or aggravated by, a microorganism on mammalian tissue (particularly, skin and/or a mucous membrane); a method of decolonizing at least a portion of the nasal cavities, anterior nares, and/or nasopharynx of a subject of microorganisms; a method of treating a middle ear infection in a subject (through the middle ear, the Eustachian tube, and/or the tympanic membrane); a method of treating chronic sinusitis in a subject (by treating at least a portion of the respiratory system, particularly the upper respiratory system, including the nasal cavities, anterior nares, and/or nasopharynx); a method of treating impetigo on the skin of a subject; a method of treating and/or preventing an infection on mammalian tissue (particularly, the skin, mucosal tissue, and/or wound) of a subject; a method of treating a burn; a method of killing or inactivating microorganisms (e.g., killing bacteria and/or fungi, or inactivating viruses); a method for providing residual antimicrobial efficacy (e.g., antibacterial, antifungal, and/or antiviral efficacy) that results from leaving a residue or imparting a condition on a surface (such as skin, mucosal tissue, wound, and/or medical device that contacts such surfaces) that remains effective and provides significant antimicrobial activity; a method of preventing and/or treating a subject for a common cold and/or respiratory affliction caused by a microbial infection; a method of decolonizing at least a portion of the throat/esophagus of a subject of microorganisms; and a method of decolonizing at least a portion of the oral cavity of a subject of microorganisms.

It should be understood that compositions of the present invention can be used in situations in which there are no clinical indications of an affliction. For example, compositions of the present invention can be used in methods of decolonizing at least a portion of the nasal cavities (i.e., space behind the vestibule of the nose), anterior nares (i.e., the opening in the nose to the nasal cavities, also referred to as the external nares), and/or nasopharynx (i.e., the portion of the pharynx, i.e., throat, that lies above the point of food entry into the pharynx) of a subject of microorganisms. A suitable model to test for the effectiveness of compositions to decolonize the anterior nares has been established and is described by K. Kiser et al., *Infect and Immunity;* 67(10), 5001-5006 (1999), which is incorporated herein by reference in its entirety. Compositions of the present invention can also be used to decolonize microorganisms from wounds.

Decolonization methods using compositions of the present invention are particularly useful in immunocompromised patients (including oncology patients, diabetics, HIV patients, transplant patients and the like), particularly for fungi such as *Aspergillus* spp. and *Fusarium* spp.

In particular, compositions of the present invention can be used in acute and chronic wounds to eliminate bacteria including methicillin-resistant *Staphylococcus aureus*, which may or may not show clinical signs of infection such as inflammation, pus, exudate, etc. Also, it is of significance to note that certain compositions of the present invention can kill lipid-enveloped viruses, which can be very difficult to kill and can cause shingles (Herpes), chronic sinusitis, otitis media, and other local diseases.

Those of ordinary skill in the art will readily determine when a composition of the present invention provides antimicrobial activity using assay and bacterial screening methods well known in the art. One readily-performed assay involves exposing selected known or readily-available viable microorganism strains, such as *Enterococcus* spp., *Staphylococcus* spp., *Streptococcus* spp., *Pseudomonas* spp., or *Salmonella* spp., to a test composition at a predetermined bacterial bioburden level in a culture medium at an appropriate temperature. For the preferred compositions of the present invention, this is most conveniently done by the Colony Biofilm Test described in the Examples section. Briefly, after a sufficient contact time, an aliquot of a sample containing the exposed bacteria is collected, diluted, and plated out on an appropriate culture medium. The plated sample of bacteria is incubated for a suitable period of time and the number of viable bacterial colonies growing on the plate is counted. Once colonies have been counted, the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure. Preferred composition of the present invention have an average of at least a 4 log reduction in test bacteria in 10 minutes.

Many of the preferred compositions were tested as described in the Examples section for antimicrobial activity against Pseudomonas aeruginosa (Gram negative, ATCC No. 15442). In general, the Pseudomonas aeruginosa is often the most difficult to kill. Preferred compositions of the present invention also exhibit very rapid antimicrobial activity. As shown in the Examples section, preferred formulations are able to achieve an average log reduction of at least 4 log against Pseudomonas aeruginosa after a 10 minute exposure and, preferably, after a 5 minute exposure. More preferred compositions are able to achieve an average log reduction of at least 5 log and even more preferred at least 6 log against these three organisms after a 10 minute exposure and preferably after a 5 minute exposure.

For residual antimicrobial efficacy, compositions of the present invention preferably maintain an average log reduction of at least 1 log, more preferably at least 1.5 log, and even more preferably at least 2 log for at least 0.5 hour, more preferably at least 1 hour, and even more preferably at least 3 hours after application to the affected site or after testing the composition on the forearm of a subject.

Thus, such compositions can be applied multiple times over one or more days to treat topical infections or to eradicate unwanted bacteria (e.g., nasal colonization of S. aureus).

Preferred compositions of the present invention contain an effective amount of (C8-12) 1,2-alkane diol to rapidly kill or inactivate microorganisms on skin, skin lesions, and mucosal membranes. In any embodiment, the (C8-12) 1,2-alkane diol comprises 1,2-octane diol. In certain embodiments, the (C8-C12) 1,2 alkane diol is present at a concentration of at least about 0.05% by weight, at least about 0.1% by weight, at least about 0.2% by weight, at least about 0.5% by weight, at least about 1.5% by weight, or at least about 2% by weight. In any embodiment, the (C8-C12) 1,2 alkane diol is present at a concentration of less than or equal to 3% by weight, less than or equal to 2% by weight, less than or equal to 1.5% by weight, less than or equal to 1.0% by weight, or less than or equal to 0.5% by weight. In certain embodiments, essentially all of the microorganisms are eradicated or inactivated within five days, preferably within three days, more preferably two days, and most preferably within 24 hours using one or more doses.

Preferred compositions of the present invention have a generally low irritation level for skin, skin lesions, and mucosal membranes (including the anterior nares, nasal cavities, nasopharyngeal cavity, and other portions of the upper respiratory tract). For example, certain preferred compositions of the present invention are no more irritating than BACTROBAN® ointment (on skin) or BACTROBAN nasal (in the anterior nares) products available from Glaxo Smith Kline.

Preferred compositions of the present invention are substantive for fairly long periods of time to ensure adequate efficacy. For example, certain compositions of the present invention remain at the site of application with antimicrobial activity for at least 4 hours and more preferably at least 8 hours.

Preferred compositions of the present invention are physically stable. As defined herein, "physically stable" compositions are those that do not significantly change due to substantial precipitation, crystallization, phase separation and the like, from their original condition during storage at 23° for at least 3 months, and preferably for at least 6 months. Particularly preferred compositions are physically stable if a 10-milliliter (10-mL) sample of the composition when placed in a 15-mL conical-shaped graduated plastic centrifuge tube (Corning) and centrifuged at 3,3000 revolutions per minute (rpm) for 10 minutes using a Labofuge™ B model 2650 centrifuge manufactured by Heraeus Sepatech GmbH, Osterode, West Germany (or similar centrifuge at 2275×g) has no visible phase separation in the bottom or top of the tube.

Preferred compositions of the present invention exhibit good chemical stability. The most preferred compositions retain an average of at least 97% of both the quaternary amine component and the 1,2 alkane diol component after aging for 4 weeks at 40° C. in a sealed container beyond an initial 5-day equilibration period at 23° C. The percent retention is understood to mean the weight percent of antiseptic component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antiseptic component is preferably determined using gas chromatography or high performance liquid chromatography.

Generally, compositions of this invention may be in one of the following forms:

A hydrophobic ointment: The compositions are formulated with a hydrophobic base (e.g., petrolatum, thickened or gelled water insoluble oils, and the like) and optionally having a minor amount of a water soluble phase.

An oil-in-water emulsion: The compositions may be in formulations in which the antimicrobial components (e.g., (C8-12) 1,2-alkane diol) is emulsified into an emulsion comprising a discrete phase of a hydrophobic component and a continuous phase that includes water and optionally one or more polar hydrophilic carrier(s) as well as salts, surfactants, emulsifiers, and other components. These emulsions may include water-soluble or water-swellable polymers as well as one or more emulsifier that helps to stabilize the emulsion. These emulsions may contain a quaternary amine antiseptic component.

Thickened aqueous compositions: These systems include an aqueous phase which has been thickened to achieve a viscosity of at least 500 centipoise (cps), more preferably at least 1,000 cps, even more preferably at least 10,000 cps, even more preferably at least 20,000 cps, even more preferably at least 50,000 cps, even more preferably at least 75,000, even more preferably at least 100,000, and even more preferably at least 250,000 cps (and even as high as 500,000 cps, 1,000,000 cps, or higher). The viscosity is determined using the Viscosity Test described herein. These systems can be thickened by suitable natural, modified natural, or synthetic polymers as described below. Alternatively, the thickened aqueous gels can be thickened using suitable polyethoxylated alkyl chain surfactants that effectively thicken the composition as well as other nonionic, cationic, or anionic emulsifier systems such as POLA- WAX™, COSMOWAX™ and CROTHIX™ as well as cationic (INCROQUAT™ Behenyl TMS) and anionic (CRODAPHOS™) systems from Croda Inc.

Hydrophilic compositions: These are systems in which the continuous phase includes at least one water-soluble hydrophilic component other than water. The formulations may optionally also contain water up to about 20% by weight. Higher concentrations may be suitable in some compositions. Suitable hydrophilic components include one or more glycols (such as glycerin, propylene glycol, butylene glycol, etc.), polyethylene glycols (PEG), random or block copolymers of ethylene oxide, propylene oxide, and/or butylene oxide, polyalkoxylated surfactants having one or more hydrophobic moieties per molecule, silicone copolyols, as well as combinations thereof. One skilled in the art will recognize that the level of ethoxylation must be sufficient to render the hydrophilic component water-soluble or water dispersible at 23° C. In some embodiments, the water content is less than 10 wt-% and more preferably less than about 5% by weight of the composition. In certain embodiments, water is present in the composition at a greater weight percent than each of the quaternary amine antiseptic component; the polycarboxylic acid chelator, if present; the alphahydroxy acid buffer, if present; and the (C8-C12) 1,2-alkane diol.

In certain embodiments, the compositions have a viscosity of at least 20 cps, preferably greater than 100 cps, more preferably greater than 1000 cps, even more preferably greater than 10,000 cps and most preferably greater than 25,000 cps when measured by the Viscosity Test described herein. Higher viscosities are preferred to reduce migration as well as to provide substantivity (resistance to removal by fluids) to ensure long-term antimicrobial activity. Most preferred compositions have viscosities in excess of 50,000 cps and most preferably in excess of 100,000 cps at 23-25° C. when measured by the Viscosity Test. Most preferred compositions meet these viscosity values even after heating to 32° C., 35° C. or as high as 37° C. to ensure when in contact with mammalian tissue the compositions remain substantive.

Quaternary Amine Antiseptic and Octenidine Component. Particularly preferred compounds of this class have one, two, three, or more C8-C18 alkyl or aralkyl chains and may be represented by the following formula:

$R^1R^2NR^3R^{4+}X^-$

Where $R^1$ and $R^2$ are C1-C18 linear or branched alkyl, alkaryl, or aralkyl chains that may be substituted in available positions by N, O, or S provided at least one $R^1$ or $R^2$ is a C8-C18 linear or branched alkyl, alkaryl, or aralkyl chains that may be substituted in available positions by N, O, or S. $R^3$ and $R^4$ are C1-C6 alkyl, phenyl, benzyl, or C8-C12 alkaryl groups. $R^3$ and $R^4$ may also form a ring such as a pyridine ring with the nitrogen of the quaternary ammonium group. X is an anion, preferably a halide, and most preferably Cl⁻ or Br⁻. Other anions may include methosulfate, ethosulfate, phosphates and the like. Preferred compounds of this class include monoalkyltrimethylammonium salts, monoalkyldimethylbenzyl ammonium salts, dialkyldimethyl ammonium salts, benzethonium chloride, and octenidine.

Nonlimiting examples of quaternary amine antiseptics suitable for use in an antiseptic composition according to the present disclosure include octenidine salt, a benzethonium salt, a C12-C18 alkylpyridinium salt, C12-C18 alkyltrimethylammonium salt, a di-(C8-C16) alkyldimethyl ammonium salt, a polyquaternary amine salt compound, an alkyldimethylbenzylammonium salt, and a combination of any two or more of the foregoing quaternary amine antiseptic components.

The quaternary amine antiseptic component is typically added to the compositions at a concentration of at least about 0.01 wt %, at least about 0.05 wt %, or at least about 0.1 by weight. Preferably, the concentration is less than or equal to 10 wt %, more preferably less than or equal to 5 wt %, and most preferably less than or equal to 1.0% by weight.

The antimicrobial components of this invention (e.g., the quaternary amine antiseptic component, the (C8-C12) 1,2-alkane diol) may be used in combination, or with other antiseptics in order to effectively kill microorganisms on tissue. Additional antiseptics for use with those described herein include peroxides; antimicrobial lipids disclosed in U.S. Pat. Nos. 8,512,723 and 10,016,501, both of which are incorporated by reference in their entirety; additional cationic antiseptics disclosed in U.S. Pat. No. 10,016,501; (C6-C14) alkyl carboxylic acids and alkyl ester carboxylic acids, antimicrobial natural oils, and compatible combinations thereof as provided in U.S. Pat. No. 8,512,723; diphenyl ethers, phenols, halogenated phenols, bisphenols, resorcinols and its derivatives, anilides, and combinations thereof.

In certain embodiments, a composition of the present disclosure comprises a polycarboxylic acid chelator to enhance the antimicrobial activity of the other antimicrobial components. The activity enhancement may be especially useful against Gram negative bacteria, such as *E. coli* and *Pseudomonas* sp. The chelator preferably affects the integrity of the cell envelope of the bacteria. While not bound by theory, it is presently believed that the chelator functions by allowing the antiseptic to more easily enter the cell cytoplasm and/or by facilitating disruption of the cell envelope and/or by disrupting microbial metabolism.

Nonlimiting examples of polycarboxylic acid chelators suitable for use in compositions of the present disclosure include citric acid or a salt thereof, succinic acid or a salt thereof, malic acid or a salt thereof, tartaric acid or a salt thereof, adipic acid or a salt thereof, ethylenediamine-N,N,N',N'-tetraacetic acid or a salt thereof, and ethylene glycol-bis(b-aminoethyl ether)-N,N,N',N'-tetraacetic acid or a salt thereof, ethylenediamine-N,N'-bis(2-hydroxyphenylaceic acid), polyphosphate salts, polyphosphonic acid salts and combinations thereof. Preferably, when EDTA is present in the composition, either the free acid or the mono- or di-salt form of EDTA is used.

In certain embodiments, an antiseptic composition of the present disclosure may comprise an alphahydroxy acid instead of (or in addition to) the polycarboxylic acid chelator. Nonlimiting examples of alphahydroxy acids suitable for use in compositions of the present disclosure include citric acid or a salt thereof, mandelic acid or a salt thereof, malic acid or a salt thereof, tartaric acid or a salt thereof, gluconic acid or a salt thereof, gluconolactone, glycolic acid or a salt thereof, and lactic acid or a salt thereof, and combinations of any two or more of the foregoing alphahydroxy acids. These acids may be in D, L, or DL form and may be present as free acid, lactone, or partial salts thereof. All such forms are encompassed by the term "acid." Preferably, at least 10% on a molar basis of the acids are present in the free acid form. More preferably, at least 25% on a molar basis of the acids are present in the free acid form. In certain preferred embodiments, the alpha-hydroxy acids useful in the compositions of the present invention are selected from the group consisting of lactic acid, mandelic acid, and malic acid, and mixtures thereof. Other suitable alpha-hydroxy acids are described in U.S. Pat. No. 5,665,776, which is incorporated herein by reference in its entirety.

Optionally, in any embodiment, a composition of the present disclosure further comprises a betahydroxy acid. Nonlimiting examples of betahydroxy acids suitable for use in compositions of the present disclosure include betahydroxypropionic acid, salicylic acid, betahydroxybutanoic acid, tropic acid, trethocanic acid, and combinations of any two or more of the foregoing betahydroxy acids.

The alphahydroxy acid and/or betahydroxy acid is preferably present in its protonated, free acid form. It is not necessary for all the alphahydroxy acids and/or betahydroxy acids to be present in the free acid form, however, the preferred concentrations listed herein refer to the amount present in the free acid form. Furthermore, the alphahydroxy acid and/or betahydroxy acid that include carboxylic acid groups is preferably present with at least one, and more preferably at least two, carboxylic acid groups in their free acid form. The concentrations given herein assume this to be the case.

One or more alphahydroxy acid and/or betahydroxy acid may be used in the compositions of the present invention at a suitable level to produce the desired result. In a preferred embodiment, they are present in a total amount greater than 0.1 wt-%, preferably in an amount greater than 0.25 wt %, more preferably in an amount greater than 0.5 wt %, even more preferably in an amount greater than 1 wt % and most preferably in an amount greater than about 2 wt % based on the total weight of the ready to use composition. In a preferred embodiment, they are present in a total amount of no greater than 10 wt-%, based on the total weight of the ready to use composition. Higher concentrations may become irritating.

The alpha-hydroxy acid and/or beta-hydroxy acid is preferably present in a concentration of no greater than 50 millimoles per 100 grams of formulated composition. In most embodiments, alphahydroxy acid, betahydroxy acid is preferably present in a concentration of no greater than 50 millimoles per 100 grams, more preferably no greater than 30 millimoles per 100 grams, and most preferably no greater than 25 millimoles per 100 grams of formulated composition.

Alpha-hydroxy Acids. An alpha-hydroxy acid is typically a compound represented by the formula:

$R^5(CR^6OH)_n COOH$, wherein: $R^5$ and $R^6$ are each independently H or a (C1-C8) alkyl group (straight, branched, or cyclic), a (C6-C12)aryl, or a (C6-C12)aralkyl or alkaryl group (wherein the alkyl group is straight, branched, or cyclic), wherein $R^5$ and $R^6$ may be optionally substituted with one or more carboxylic acid groups; and n=1-3, preferably, n=1-2.

Beta-hydroxy Acids. A beta-hydroxy acid is typically a compound represented by the formula:

$R^7(CR^8OH)_n(CHR^9)_m COOH$ or

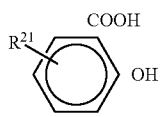

wherein: $R^7$, $R^8$, and $R^9$ are each independently H or a (C1-C8)alkyl group (saturated straight, branched, or cyclic group), a (C6-C12)aryl, or a (C6-C12)aralkyl or alkaryl group (wherein the alkyl group is straight, branched, or cyclic), wherein $R^7$ and $R^8$ may be optionally substituted with one or more carboxylic acid groups; m=0 or 1; n=1-3 (preferably, n=1-2); and wherein R is H, (C1-C4)alkyl, or a halogen).

Optionally, compositions of the present invention can include a hydrophilic or water-soluble component to help solubilize and/or physically stabilize the polycarboxylic acid chelator, if present, and/or the alphahydroxy acid buffer in the composition and/or to enhance the antimicrobial efficacy and/or the speed of antimicrobial efficacy. Incorporation of a sufficient amount of hydrophilic component in hydrophobic ointments can increase the antimicrobial activity both in terms of speed of kill and extent of kill. While not intended to be bound by theory, the incorporation of the hydrophilic component may allow more of the (C8-C12) 1,2-alkane diol to be available at the surface or to more rapidly diffuse to the surface of an ointment form of the composition during use.

Certain compositions may be solutions, emulsions (one liquid/gel/paste dispersed in another liquid/gel/paste), dispersions (solid in liquid/gel/paste), or combinations thereof.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limits above and typically have no alkyl chains of greater that C6 and usually no greater than C4), N-methylpyrrolidone, alkyl esters (i.e., having a sufficiently small number of carbon atoms to meet the solubility limit above and typically have no alkyl chains of greater than C6 and usually no greater than C4), as well as combinations thereof. Preferably, the hydrophilic components include polyhydric alcohols, lower alkyl ethers, and short-chain esters. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to glycerol, polypropylene glycol, dipropylene glycol, tripropylene glycol, polypropylene glycol, polyethylene glycol, diethylene glycol, pentaerythritol trimethylolpropane, trimethylolethane, trimethylolbutane, sorbitol, maltitol, xylitol, pantothenol, ethylene glycol adducts of polyhydric alcohol, propylene oxide addicts of polyhydric alcohol, 1,3-butanediol, diglycerine, polyglycerine, erythritol, sorbitan sugars (e.g., sucrose, glucose, fructose, maltose, xylose, saccharose, trehalose), sugar alcohols, and the like. Certain preferred polyhydric alcohols include glycols (i.e., including those containing two hydroxyl groups) including glycerin and propylene glycol. Certain other preferred polyhydric alcohols include sucrose, xylitol, mannitol, and sorbitol.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, methyl lactate, ethyl lactate esters, esters of polyethoxylated glycols, and combinations thereof.

In certain preferred embodiments, the hydrophilic components useful in the compositions of the present invention include those selected from the group consisting of glycols, and in particular glycerin and propylene glycol, and mixtures thereof.

In certain preferred embodiments, the hydrophilic component is present in a total amount of no greater than 75 wt-%, preferably no greater than 60 wt-% more preferably no greater than 50 wt-% even more preferably no more than 30 wt-% based on the ready-to-use composition. When the hydrophilic component is present in the greatest amount relative to the other components of the composition, it is referred to as a "vehicle".

For certain applications, it may be desirable to formulate the (C8-C12) 1,2-alkane diol in compositions including a hydrophilic component vehicle that is thickened with soluble, swellable, or insoluble (e.g. insoluble) organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres sue as those available under the trade-names "ZEOSPHERES" or "Z-LIGHT" from 3M Company, St. Paul, Minn. The above fillers can be used alone or in combination.

In certain preferred embodiments with relatively lower water content, the water is preferably present in an amount less than 20 wt-%, preferably less than 10 wt-%, more preferably less than 5 wt-%, and even more preferably less than 2 wt-%, based on the ready-to-use composition. This helps the chemical stability of the composition and may reduce irritation. For certain other embodiments, water can be used in a much greater amount, and can even be the primary component, as long as the composition is highly viscous. Preferably such highly-viscous compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). in the viscosity can be measured as described below in the Viscosity Test. Most preferred compositions meet these viscosity values even after heating to 32° C. or even 35° C., or as high as 37° C. to ensure when in contact with mammalian tissue the compositions remain substantive.

In some embodiments of the present invention, the compositions have a viscosity of at least 20 cps, preferably at least 100 cps when measured by the Viscosity Test described herein. Higher viscosities are preferred to reduce migration as well as to provide substantivity (resistance to removal by fluids) to ensure long-term antimicrobial activity.

Hydrophobic Component. Certain preferred compositions of the present invention also include one or more hydrophobic materials. A hydrophobic material is typically an organic compound, which at 23° C. is a liquid, gelatinous, semisolid, or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, short chain (i.e., C1-C6) alkyl or C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or diols optionally substituted in available positions by —OH; (C2-C18)alkyl or (C6-C12) aryl esters of glycerol, pentaerythritol, ethylene glycol, propylene glycol, as well as polyethoxylated derivatives of these; (C12-C22) alkyl esters or (C12-C22) ethers of polypropylene glycol; (C12-C22) alkyl esters or (C12-C22) ethers of polypropylene glycol/polyethylene glycol copolymer; and polyether polysiloxane copolymers. Additional examples of hydrophobic components include cyclic dimethicones, including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22) alkyl and (C12-C22) alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, sesame oil, safflower oil, soybean oil, and the like, and blends thereof. In certain preferred embodiments, the hydrophobic components useful in the compositions of the present invention include those selected from the group consisting of petrolatum USP and short chain (C1-C6) alkyl or C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or diols optionally substituted in available positions by —OH (such as diisopropyladipate, diisopropylsebacate); (C1-C9) alkyl or (C6-C12) aryl esters of glycerol, pentaerythritol, ethylene glycol, propylene glycol (such as glyceryl tricaprylate/caprate); and mixtures thereof. For certain particularly preferred embodiments, the hydrophobic component is petrolatum.

One or more hydrophobic materials may be used in the compositions of the present invention at a suitable level to produce the desired result. In a preferred embodiment (in which the compositions include very little or no water), the hydrophobic component is present in a total amount of at least 50 wt-%, more preferably at least 70 wt-%, and even more preferably at least 80 wt-%, based on the ready to use composition. In a preferred embodiment, the hydrophobic component is present in a total amount of no greater than 99 wt-%, more preferably no more than 95 wt-%, and even more preferably no more than 92 wt-%, based on the ready to use composition. When the hydrophobic component is present in the greatest amount, it is referred to as a "vehicle". In those formulations where the hydrophobic component(s) are present in the same concentrations, the continuous phase is referred to as the "vehicle".

Optional Additives. Compositions of the present invention may additionally employ adjunct components conventionally found in pharmaceutical compositions in their art-established fashion and at their art-established levels. Thus, for example, the compositions may contain additional compatible pharmaceutically-active materials for combination therapy (such as supplementary antimicrobials, anti-parasitic agents, antipruritics, astringents, local anesthetics, steroids, non-steroidal anti-inflammatory agents, or other anti-inflammatory agents), or may contain materials useful in physically formulating various dosage forms of the present invention, such as excipients, dyes, perfumes, lubricants, thickening agents, stabilizers, skin penetration enhancers, preservatives, or antioxidants.

In certain embodiments, a composition of the present disclosure can optionally comprise an alcohol (e.g., ethanol) to promote dissolution of one or more of the components and to inhibit growth of fungal microorganisms.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will be appreciated that additional antiseptics, disinfectants, or antibiotics may be included and are contemplated. These include, for example, addition of metals such as silver, copper, zinc; iodine and iodophors; chlorhexidine and its various salts such as chlorhexidine digluconate; alexidine, polyhexamethylene biguanide, polychlorometaxylenol, triclosan, antimicrobial quaternary amines including polymeric quaternary amines, "azole" antifungal agents including chlortrimazole, miconazole, econazole, ketoconazole, and salts thereof, and the like. Antibiotics such as neomycin sulfate, bacitracin, mupirocin, polymyxin, rifampin, tetracycline, and the like, also may be included. Preferred compositions, however, are free of antibiotics due to the chance of resistance formation.

Formulations and Methods of Preparation

Many of the compositions of the present invention have exceptional broad spectrum antimicrobial activity and thus are generally not terminally sterilized but, if necessary, may be sterilized by a variety of industry-standard techniques. For example, it may be preferred to sterilize the compositions in their final packaged form using electron beam. It may also be possible to sterilize the sample by gamma radiation or heat. It may also be possible to sterilize the sample by steam using a device such as autoclave or by holding the formulation at a substantially lower temperature e.g. 60-70° C. for a time sufficient to sterilize the contents. Other forms of sterilization may be acceptable. It may also be suitable to include preservatives in the formulations to prevent growth of certain microorganisms. Suitable preservatives include industry-standard compounds such as parabens (methyl, ethyl, propyl, isopropyl, isobutyl, etc.), 2-bromo-2-nitro-1,3,diol; 5-bromo-5-nitro-1,3-dioxane, chlorbutanol, diazolidinyl urea, iodopropynyl butylcarbamate, phenoxyethanol, phenethyl alcohol, benzyl alcohol, benzoic acid, sorbic acid, halogenated cresols, methylchlorothazolinone, and the like, as well as combinations of these compounds.

The compositions of the present invention preferably adhere well to mammalian tissues (particularly skin, mucosal tissue, and wounds) in order to deliver antimicrobial activity to the intended site over a long period even in the presence of perspiration, drainage (e.g., mucosal secretions), or mild lavage. The compositions can be non-aqueous, although high viscosity compositions can include a large amount of water. The component in the greatest amount (i.e., the vehicle) in the formulations of the invention may be any conventional vehicle commonly used for topical treatment of human or animal skin. The formulations are typically selected from one of the following three types: (1) anhydrous or nearly-anhydrous formulations with a hydrophobic vehicle (i.e., the hydrophobic component, which can include one or more hydrophobic compounds, is present in the greatest amount); (2) anhydrous or nearly-anhydrous formulations with a hydrophilic vehicle (i.e., the hydrophilic component, which can include one or more hydrophilic compounds, is present in the greatest amount); and 3) highly viscous water-based formulations. These are discussed below.

(1) Anhydrous or Nearly Anhydrous Formulations with a Hydrophobic Vehicle: In certain preferred embodiments of the present invention, the compositions include a (C8-C12) 1,2-alkane diol; a quaternary amine antiseptic component; and a polycarboxylic acid chelator or an alphahydroxy acid buffer in a hydrophobic vehicle with a small amount of a hydrophilic component. For example, when formulating with certain solid surfactants or certain antiseptics in petrolatum or other hydrophobic vehicle many antiseptics, and surfactants will dissolve into the petrolatum at temperatures above 85° C.; however, upon cooling, the antiseptic and/or surfactant crystals precipitate back out of solution making it difficult to produce a uniform formulation. If at least 0.1 wt-%, and preferably at least 1.0 wt-%, more preferably at least 5 wt %, and most preferably at least 10 wt-% of a hydrophilic compound (e.g., a glycol) is added a stable formulation can be obtained. It is believed that these formulations produce an emulsion in which the antiseptic components and/or surfactant is dissolved, emulsified, or dispersed in the hydrophilic component which is emulsified into the hydrophobic component(s). These compositions are stable upon cooling and centrifuging.

These formulations can be manufactured with relative ease by first heating the hydrophobic component, if present, to 85° C., adding in the hydrophilic component, the quaternary amine antiseptic component, and the polycarboxylic acid chelator and/or alphahydroxy acid buffer; cooling to 65° C., and adding the (C8-C12) 1,2-alkane diol. Alternatively, the quaternary amine and the polycarboxylic acid chelator and/or alphahydroxy acid can be pre-dissolved in the hydrophilic component (optionally along and added to the hydrophobic component either before or after addition of the (C8-C12) 1,2-alkane diol. If either the (C8-C12) 1,2-alkane diol or the hydrophobic component is solid at room temperature, this is done at the minimum temperature necessary to ensure dissolution and uniformity of the composition.

(2) Water in Oil Emulsions: The (C8-C12) 1,2-alkane diol of this invention can be formulated into water-in-oil emulsions in combination with the quaternary amine antiseptic component, and the polycarboxylic acid chelator and/or alphahydroxy acid buffer. Particularly preferred compositions comprise at least 35 wt-%, preferably at least 40 wt-%, more preferably at least 45 wt-% and most preferably at least 50% by weight oil phase. As used herein the oil phase is comprised of all components which are either insoluble in water or preferentially soluble in the oil(s) present at 23° C. Generally speaking the hydrophobic component (oil) is mixed in a first container along with any emulsifier(s) optionally including polymeric emulsifiers and heated to a temperature sufficient to ensure a homogenous composition and subsequent stable emulsion. The temperature is typically raised to at least 60° C., preferably to at least 80° C. and more preferably to 100° C. or more. In a separate second container, the hydrophilic ingredients are mixed, including one or more of the following: water, hydrophilic component, surfactant(s), and acids/bases to adjust the pH of the final composition. The contents of the second container are heated to a temperature sufficient to ensure a stable final emulsion composition without significantly degrading any of the components, typically greater than 40° C., preferably greater than 50° C. and more preferably to greater than 60° C. While hot, the second container is added to the first container using a high shear mixer. The composition may be continuously mixed until cool (T<40° C.) or it can be allowed to sit if the contents remain uniformly mixed. If the antiseptic is heat sensitive, it is added with mixing during the cooling down period. If it is not heat sensitive, it may be added to either container. The viscosity of these compositions may be adjusted by altering the levels of emulsifier; changing the ratio of water to oil phase; selection of the oil phase (e.g., select an oil (hydrophobic component) which is more or less viscous); incorporation of a polymeric or particulate thickener, etc.

(3) Hydrophilic Vehicle: Antiseptic components of this invention can be formulated into a hydrophilic component such as that based on the hydrophilic compounds discussed above optionally in combination with the quaternary amine antiseptic component, and the polycarboxylic acid chelator and/or alphahydroxy acid buffer. Particularly preferred are polyethylene glycols (PEGs), glycols, and combinations thereof, including blends of different molecular weight PEGs optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

In certain preferred embodiments of the present invention, the compositions are in the form of an ointment or cream. That is, the compositions are in the form of a relatively viscous state such that they are suitable for application to nasal passageways.

(4) Water-based Formulations: Aqueous compositions of the present invention are those in which water is present in the greatest amount, thereby forming the "vehicle." For these systems it is particularly important that a relatively high viscosity be imparted to the composition to ensure that the antimicrobial composition is not rapidly dispersed off the treated area. These formulations also adhere well to tissue and thus deliver the antiseptic to the intended site over a prolonged period even in the presence of perspiration, drainage (e.g., mucosal secretions), or mild lavage. Such a high viscosity can be imparted by a thickener system. The thickener system of the invention is compatible with the antiseptic composition described above in order to provide suitable antimicrobial efficacy, chemical and physical stability, acceptable cosmetic properties, and appropriate viscosity for retention in the afflicted area.

Preferred thickener systems used in the compositions of the present invention are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

The antimicrobial compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The neat antiseptic compositions according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Inhaled medications are preferred in some embodiments because of the direct delivery to the lung. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components that will not significantly impair the biological properties of the agent (see, for example, Sciarra and Cutie, "Aerosols," in Remington's Pharmaceutical Sciences, 18th edition, 1990, pp. 1694-1712), which is incorporated herein by reference in its entirety.

The compounds may also be formulated in rectal or vaginal compositions such as suppositories or retention enemas, e.g., containing conventional suppository bases such as cocoa butter or other glycerides.

Viscosity

Certain compositions of the present invention have a viscosity of at least 500 Centipoise (cps) for ease of application topically. More preferably, compositions of the present invention have a viscosity of at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as about 500,000 cps, 1,000,000 cps, or more). The viscosity can be measured as described below in the Viscosity Test. Preferred formulations have high viscosity even after application to mammalian tissue at 32-37° C. Because certain optional ingredients, such as hydrophilic compounds, hydrophobic compounds, and the like, may affect the viscosity (either positively or negatively), the measured viscosity is that of the final composition.

Lower viscosity compositions can be used, however, in certain applications, such as for the treatment of middle ear infection and chronic sinusitis. For example, afflictions of the middle ear (e.g., otitis media or infection of the middle ear) may be treated with compositions of the present invention having a viscosity lower than 1000 cps, or lower than 100 cps, or lower than 25 cps, more readily by administration through the outer ear or through the nose and into the Eustachian tubes. The viscosity is measured by the Viscosity Test described herein.

Delivery Methods and Devices

Topical antimicrobial treatment regimens according to the practice of this invention include applying a safe and effective amount of the compositions described herein directly to the infected or at-risk skin, wound, or mucous membrane; particularly, the nasal nares and passages that are particularly susceptible to microbial contamination.

Compositions of the present invention can be delivered using a variety of techniques. Typically, the compositions are delivered to the skin and/or mucosal tissue in a manner that allows them to penetrate into the skin and/or mucosal tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

In the methods of the present invention, the antiseptic compositions may be provided as a formulation suitable for delivery to mammalian tissue (e.g., skin and/or mucosal surfaces). Suitable formulations can include, but are not limited to, creams, gels, foams, ointments, lotions, balms, waxes, salves, solutions, suspensions, dispersions, water in oil or oil in water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5) alkanes as well as nitrous oxide and dimethyl ether.

If delivered as a foam, the composition may be dispensed from an aerating dispenser such as the F2 Finger Pump Foamer available from Air Spray International Pompano Beach, FL Alternatively, the foam may be generated using a suitable propellant such as those described above.

In some embodiments, compositions of the present invention can be formulated into various consumer products such as deodorants, shampoos, shower gels, detergents, household cleaning products, etc.

For very high viscosity formulations the composition may be delivered in essentially a solid dosage form by placing the composition in or on the tissue to be treated. For example, a small suppository type delivery could be placed into the anterior nares for eradication of *Staphylococcus* sp.

Various other modes of administration can be used as well known to one of skill in the art depending on the desired location for contact of the antimicrobial compositions of the present invention. For example, afflictions of the middle ear (e.g., otitis media or infection of the middle ear) may be treated with compositions of the present invention by administration through the nose and into the Eustachian tubes or they can be instilled directly into the middle ear through the tympanic membrane. The formulations may traverse the tympanic membrane with the aid of a syringe or do so by diffusion. Penetration enhancers may be used to enhance diffusion across the tympanic membrane.

For application to skin or mucosal tissue, for example, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the nose or other topical tissue, the composition could be dispensed directly from a tube and spread by a number of means including squeezing the outside of the nose together repeatedly, wiping with the tip of the tube or with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. Therefore, in most instances, applicator devices such as webs and swabs are coated on the applicator web at greater than 50% by weight of the dry web and preferably in excess of 100% by weight of the dry web (on a swab, this would include the weight only of the web).

The collapsible containers may be made in a number of single layer, laminate, or coextruded constructions. Materials of construction may include polyolefins such as low, medium or high density polyethylene including low and linear low density polyethylene, polypropylene, as well as copolymers of ethylene and/or propylene with other polar or non-polar comonomers; polyamides such as nylons, polyesters such as polyethylene terephalate, polybutyleneterephalate, polyethylenenaphthalate; polyurethanes, polyacrylates, and the like. In some constructions it may be desirable to include a barrier material to prevent evaporation of one or more components of the formulation. Suitable barrier materials include polyesters (e.g., polyethylene terephthalate, polyethylene naphthalate and polybutylene terephalate and the like), fluorinated layers such as polytetrafluoroethylene (PTFE, e.g., TEFLON), polyamides (e.g., nylon), chlorotriflouroethylene (ACLAR), polyvinylidene fluoride, as well as copolymers of perflourinated monomers with partially fluorinated monomers such as copolymers of tetraflouroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where x=0.5-2 and preferably 1-2) coated thermoplastics, and ceramic coated PET (CERAMIS available from CCL Container/Tube Division, Oak Ridge, NJ).

Compositions of the present invention may be applied to a mucosal surface with the use of a delivery device such as cervical caps, diaphragms and solid matrices such as tampons, cotton sponges, cotton swabs, foam sponges, and suppositories.

Accordingly, compositions of the present invention can also be delivered from cloth, sponges, paper products (e.g., paper towels, towelettes, and wipes), tampons, undercast padding, and dental floss, for example.

In some embodiments, an applicator may be used to place the device and/or antimicrobial composition in the proper location, for example, on the mucosal surface of a vagina, nasal cavity, rectum, or the like. Examples of such applicators include, for example, cardboard or plastic tube applicators commonly used for inserting tampons or suppositories.

The compositions of the present invention can be delivered from various substrates for delivery to the tissue. For example, the compositions can be delivered from a wipe or pad which when contacted to tissue will deliver at least a portion of the composition to the tissue. For application to nasal cavities the compositions may be provided by a non-woven swab such as a "Q-tip" brand cotton swab, into a foam tip applicator, and the like. The substrate may be used to deliver the composition essentially instantaneously or may be left in contact with the tissue. For example, a substrate in a tubular form could be delivered to the anterior nares using a suitable applicator and left in the anterior nares. The annular nature of the device is designed to allow delivery of the active while allowing the patient to freely breath through the nose.

Also, compositions of the present invention can be coated onto medical devices that contact skin, mucous membranes, wounds, etc. Examples of such devices include catheters such as urinary tract catheters and vascular access catheters.

A composition of the present disclosure can be used to irrigate a wound immediately after making an incision at a surgical site and/or during or prior to closure of the surgical site. The composition can be used to wet all tissue surfaces uniformly. In other embodiments, the composition may be used to wet the surface of an implant just before introduction into the surgical cavity, e.g. in a knee replacement procedure.

Topical antimicrobial treatment regimens according to the practice of this invention include applying a safe and effective amount of the compositions described herein directly to the infected or at-risk skin, wound, or mucous membrane; particularly, the nasal nares and passages that are particularly susceptible to microbial contamination. Compositions of the present invention can be delivered using a variety of techniques. Typically, the compositions are delivered to the skin and/or mucosal tissue in a manner that allows them to penetrate into the skin and/or mucosal tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

If a composition of the present invention includes certain poloxamer block copolymers of ethylene oxide and propylene oxide generally having greater than 60 mol-% polyethylene oxide (such as those available under the trade names PLURONIC F127 and F108 from BASF Corp.), as well as certain modified cellulose polymers, and is applied topically, for example, thermally induced gelation can occur. Thus, various components can be selected for use in compositions of the present invention to produce a desired effect.

The dose and frequency of application will depend on many factors including the condition to be treated, the concentration of antimicrobial components, the microbe to be killed, etc. Typically, the compositions will be delivered in dosages of at least 10 milligrams per square centimeter (mg/cm$^2$) of tissue, preferably at least about 20 mg/cm$^2$ of tissue, more preferably at least about 30 mg/cm$^2$ of tissue, and most preferably at least 50 mg/cm$^2$ of tissue, for most applications. Application can be made once, or several (e.g., 2-4) times daily for one or more days. Typically, the composition is applied 1 or 2 times/day for 1-7 days. For example, decolonization of the anterior nares may require a dose of 0.25 gram (g) per nares applied 1-3 times per day for 1-5 days. Treatment of impetigo may require 0.5 g/15 cm$^2$ (33 mg/cm$^2$ of tissue) applied 1-3 times/day for 3-10 days.

Viscosity Test

The viscosity of antimicrobial compositions according to the present disclosure can be measured at approximately 22° C. at ambient pressure using a Brookfield LVDV-I$^+$ viscometer equipped with a model D Brookfield heliopath and LV spindles. The spindle and speed is chosen for each particular sample such that the viscometer is operating in the middle of its range. All samples are allowed to equilibrate at approximately 22° C. for 24 hours prior to measurement. Preferably the viscosity is taken at the lowest speed possible while staying within 20-80% of the viscometer range and more preferably between 30-70% of the range. In all cases the sample size and container geometry are chosen to ensure that there are no wall effects. By "wall effects" it is meant the viscosity value is not affected by the container and is essentially equivalent to the viscosity taken in an infinitely large container. For this reason, lower viscosity samples may require a larger sample size to accommodate the larger spindles. The viscosity of each sample is taken as the highest relatively stable reading achieved on the first path the spindle traverses using the heliopath adapter.

EXEMPLARY EMBODIMENTS

Embodiment A is an antiseptic composition, comprising:
a quaternary amine antiseptic component and/or octenidine having a concentration of at least about 0.04% by weight;
a polycarboxylic acid chelator having a concentration of at least about 0.05 M or an alphahydroxy acid buffer having a concentration of at least about 0.05 M;
a (C8-C12) 1,2 alkane diol; and
water;
wherein the composition has a pH that is greater than or equal to 3.5 and less than 5.5 at 23° C.;
wherein the water is present in the composition at a greater weight percent than each of the quaternary amine antiseptic component; the polycarboxylic acid chelator, if present; the alphahydroxy acid buffer, if present; and the (C8-C12) 1,2-alkane diol.

Embodiment B is an antiseptic composition, comprising:
a quaternary amine antiseptic component and/or octenidine having a concentration of at least about 0.04% by weight;
a polycarboxylic acid chelator having a concentration of at least about 0.05 M or an alphahydroxy acid buffer having a concentration of at least about 0.05 M;
a (C8-C12) 1,2 alkane diol; and optionally, water;
wherein the water is present in the composition from 0% to about 75% by weight;
wherein, when the composition comprises ≥50% water by weight, the composition has a pH that is greater than or equal to 3.5 and less than 5.5 at 23° C.;
wherein when the composition comprises ≤50% water by weight, a diluted composition, made by diluting the composition 1:1 (w/w) with deionized water and thoroughly mixing, has a pH that is greater than or equal to 3.5 and less than 5.5 at 23° C.

Embodiment C is an antiseptic composition, comprising:
a quaternary amine antiseptic component and/or octenidine having a concentration of at least about 0.04% by weight;
a polycarboxylic acid chelator having a concentration of at least about 0.05 M or an alphahydroxy acid buffer having a concentration of at least about 0.05 M;
a (C8-C12) 1,2 alkane diol; and water;
wherein the composition has a pH that is greater than or equal to 3.5 and less than 5.5 at 23° C.;
wherein the water is present in the composition at a greater weight percent than any other component of the composition.

Embodiment D is the antiseptic composition of any one of the preceding Embodiments, wherein the quaternary amine and octenidine antiseptic component is selected from the group consisting of an octenidine salt, a benzethonium salt, a C12-C18 alkylpyridinium salt, C12-C18 alkyltrimethylammonium salt, a di-(C8-C16) alkyldimethyl ammonium salt, a polyquaternary amine salt compound, an alkyldimethylbenzylammonium salt, a benzalkonium halide, a benzethonium halide, octenidine dihydrohalide, and a combination of any two or more of the foregoing quaternary amine antiseptic components.

Embodiment E is the antiseptic composition of any one of the preceding Embodiments, wherein the polycarboxylic acid chelator is selected from the group consisting of citric acid or a salt thereof, succinic acid or a salt thereof, malic acid or a salt thereof, tartaric acid or a salt thereof, adipic acid or a salt thereof, ethylenediamine-N,N,N',N'-tetraacetic acid or a salt thereof, and ethylene glycol-bis(b-aminoethyl ether)-N,N,N',N'-tetraacetic acid or a salt thereof, ethylenediamine-N,N'-bis(2-hydroxyphenylacetic acid), polyphosphate salts, polyphosphonic acid salts and combinations thereof.

Embodiment F is the antiseptic composition of any one of the preceding Embodiments, wherein the alphahydroxy acid is selected from a group consisting of citric acid or a salt thereof, mandelic acid or a salt thereof, malic acid or a salt thereof, tartaric acid or a salt thereof, gluconic acid or a salt thereof, gluconolactone, glycolic acid or a salt thereof, and lactic acid or a salt thereof, and combinations of any two or more of the foregoing alphahydroxy acids.

Embodiment G is the antiseptic composition of any one of the preceding Embodiments, further comprising a betahydroxy acid.

Embodiment H is the antiseptic composition of Embodiment G, wherein the betahydroxy acid is selected from the group consisting of betahydroxypropionic acid, salicylic acid, betahydroxybutanoic acid, tropic acid, and trethocanic acid.

Embodiment I is the antiseptic composition of any one of the preceding Embodiments, wherein the quaternary ammonium antiseptic component has a concentration of about 0.010% to about 1.0% by weight.

Embodiment J is the antiseptic composition of any one of the preceding Embodiments, wherein the polycarboxylic acid chelator, if present, has a concentration of about 0.5% to about 25% by weight.

Embodiment K is the antiseptic composition of any one of the preceding Embodiments, wherein the alphahydroxy acid buffer, if present, has a concentration up to about 10% by weight.

Embodiment L is the antiseptic composition of any one of the preceding Embodiments, wherein the (C8-C12) 1,2 alkane diol is present at a concentration of about 0.05% by weight to about 3% by weight.

Embodiment M is the antiseptic composition of any one of the preceding claims, wherein the (C8-C12) 1,2 alkane diol comprises 1,2-octane diol.

Embodiment N is a method of treating a wound, the method comprising applying the composition of any one of the preceding claims to a wound site.

Embodiment O is the antiseptic composition of any one of the preceding Embodiments, wherein the composition has a pH that is greater than or equal to 3.8 and less than 5.0 at 23° C.

EXAMPLES

Materials

| Ingredients | Name | Vendor |
|---|---|---|
| Glycerol | Glycerol | Cargill Corporation, Wayzata, MN |
| Benzalkonium Chloride | BAC | Sigma Aldrich; St. Louis, MO |
| Jeecide CAP | Caprylyl Glycol or CAP | Jeen International; Fairfield, NJ |
| Water Sterile | Water | Rocky Mountain Biologicals, Inc. Missoula, Montana |
| Sodium Citrate (trisodium salt dihydrate) | Sodium Citrate | Sigma Aldrich; St. Louis, MO |
| Citric Acid Monohydrate | Citric Acid | Sigma Aldrich; St. Louis, MO |
| Natrosol ™ 250 HHX | 250 HHX | Ashland Inc.; Covington, KY |
| Cross Linked Polyvinylpyrrolidone K 90 | PVP K90 | Ashland Inc., Covington, KY |
| Ethylenediaminetetraacetic acid dipotassium salt dihydrate | EDTA | Alfa Aesar; Haverhill, MA |

All other chemicals used in the Examples were reagent-grade unless otherwise noted.

pH Measurements

All pH measurements were done using an Orion Star™ A214PH/ISE Meter from Thermo Scientific™ (Waltham, MA) using their standard procedure of calibration before each measurement. One gram of each sample composition was placed into individual 20 mL glass vials. Nine milliliters of sterile deionized water was added to each vial and the resulting mixtures were stirred under magnetic stirring overnight. The pH was measured the following day.

Colony Biofilm Test

*Pseudomonas aeruginosa* (obtained from American Type Culture Collection, strain number 15442) was grown to stationary phase overnight in tryptic soy broth (Becton, Dickenson, and Company, Franklin Lakes, NJ) at 37° C. Then 10 microliters of the overnight culture was placed in a single drop onto sterile polycarbonate membranes (25 millimeter diameter, 0.2 micrometer pore size, 5 polycarbonate filter membranes obtained from Whatman, Kent, United Kingdom) placed on top of tryptic soy agar (TSA) containing 1.5 percent agar (Becton, Dickenson, and Company, Franklin Lakes, NJ). The bacteria were allowed to grow for 24 hours at 37° C. After the growth period, the filters were aseptically transferred to TSA poured into sterile, polystyrene, 6-well plates. When applicable, a sterile silicone rubber ring with a 16 mm diameter opening was then placed around the biofilm to contain flowable materials.

The bacteria were then covered with 200 microliters of thickened gel material, or a 22-millimeter diameter disk of the example article, and incubated for 20 hours at 37° C. Each sample was tested in triplicate. Both the membranes covered in bacteria and the test material were then transferred into 10 milliliters of Dey/Englay (D/E) neutralizing broth (Becton, Dickenson, and Company, Franklin Lakes, NJ) for thickened gel material, or 20 milliliters of D/E for disks of the example article. The samples were sonicated for 1 minute in a sonicating water bath (Model 2150 from Branson Ultrasonics Corporation, Danbury, CT) and then mixed on a vortex mixer at maximum speed for 3 minutes. The samples were then serially diluted 10-fold in sterile Butterfield's phosphate buffered water and samples were plated onto AC Petri film culture medium obtained from 3M, St. Paul, MN under trade designation "3M PETRIFILM™ Aerobic Count Plates". The 3M PETRIFILM plates were incubated for 48 hours at 37° C., the number of surviving colony forming units (CFU) were enumerated, and the average log reduction value ("LRV") was calculated by subtracting the average log (CFU/sample) of the treated samples from the average log (CFU/sample) of the untreated samples.

Landrum, S.C.). The BAC solution, CAP, and water were charged into a max 100 ml Flacktek cup ("cup 1") and mixed at 2500 rpm for 30 seconds. After this time sodium citrate, and citric acid were charged into the cup 1 and mixed for an additional 30 seconds at 2500 rpm. In a max 40 ml Flacktek cup ("cup 2"), the glycerol and the HHX were mixed at 2500 rpm for 30 seconds and were subsequently transferred to cup 1. The resulting composition in cup 1 was mixed at 2500 rpm for 1 minute. The mixture was kept at least overnight before it was tested for pH and antimicrobial activity.

TABLE 2

Composition of Examples 1-8. Values for each component are listed in grams (g).

| Component | 1 | 2 | 3 | 4 | 5 | 6 | 7 | 8 |
|---|---|---|---|---|---|---|---|---|
| Glycerol | 10 | 10 | 10 | 10 | 44.53 | 45.43 | 10 | 10 |
| Natrosol ™ 250 HHX | 2.5 | 2.5 | 2.5 | 2.5 | — | — | 3 | 3 |
| BAC (50% in water) | 0.16 | 0.26 | 0.02 | 0.16 | 0.26 | 0.26 | 0.12 | 0.26 |
| Jeecide CAP | 0.5 | 0.3 | 0.45 | 0.2 | 0.5 | 0.5 | 0.1 | 0.50 |
| Water | 85.22 | 84.76 | 85.09 | 83.64 | — | — | 83.38 | 83.38 |
| Sodium Citrate | 0.92 | 1.25 | 1.11 | 2.0 | — | — | 2 | — |
| Sodium Citrate (25 wt % in water) | — | — | — | — | 4.8 | 2.4 | — | — |
| Citric acid Monohydrate | 0.7 | 0.93 | 0.83 | 1.5 | — | — | 1.5 | — |
| Citric acid Monohydrate (50 wt % in water) | — | — | — | — | 1.8 | 0.9 | — | — |
| Succinic Acid | — | — | — | — | — | — | — | 2.01 |
| NaOH (50 wt % in water) | — | — | — | — | — | — | — | 0.85 |
| Crosslinked PVP K90 (11 wt % in water) | — | — | — | — | 52.91 | 52.91 | — | — |

TABLE 3

Composition of Examples 9-16. Values for each component are listed in grams (g).

| Component | 9 | 10 | 11 | 12 | 13 | 14 | 15 | 16 |
|---|---|---|---|---|---|---|---|---|
| Glycerol | 10 | 10 | 10 | 10 | 10 | 10 | 10 | 45 |
| Natrosol ™ 250 HHX | 3 | 3 | 3 | 3 | 3 | 3 | 3 | — |
| BAC (50% (w/w) aqueous solution) | 0.26 | 0.26 | 0.26 | 0.26 | 0.26 | 0.26 | 0.26 | 0.26 |
| Jeecide CAP | 0.5 | 0.5 | 0.5 | 0.5 | 0.5 | 0.5 | 0.5 | 0.5 |
| Water | 84.29 | 82.53 | 83.27 | 81.38 | 84.21 | 83.06 | 81.14 | — |
| Citric Acid | 1.52 | — | — | — | — | — | — | — |
| Tartaric Acid | — | — | — | 2.51 | — | — | — | — |
| Crosslinked PVP K90 (11 wt % in water) | — | — | — | — | — | — | — | 50.76 |
| NaOH (50 wt % in water) | 0.43 | 0.43 | 0.96 | 2.35 | — | 0.68 | 1.82 | 1.47 |
| Gluconic Acid (50 wt % in water) | — | 3.28 | — | — | — | — | — | — |
| Gluconic Acid sodium salt | — | — | — | — | — | — | 3.28 | — |
| Lactic Acid (85 wt % in water) | — | — | 2.01 | — | — | — | — | — |
| EDTA dipotassium salt dihydrate | — | — | — | — | 2.03 | — | — | — |
| Adipic Acid | — | — | — | — | — | 2.5 | — | — |
| Succinic Acid | — | — | — | — | — | — | — | 2.01 |

Example 1

Procedure: A mixture of the ingredients listed in Table 2 was prepared using a DAC 400 FVZ SPEEDMIXER dual asymmetric centrifuge mixer (obtained from Flacktek, Inc.;

Example 2

Procedure: A mixture of the ingredients listed in Table 2 was prepared with a procedure similar to Example 1. The BAC solution, the CAP, and the water were charged into cup 1 and mixed at 2500 rpm for 30 seconds. After this time, the sodium citrate and the citric acid were charged into cup 1 and mixed for an additional 30 seconds at 2500 rpm. In cup 2, the glycerol and the HHX were mixed at 2500 rpm for 30 seconds and subsequently transferred to cup 1. The resulting composition in cup 1 was mixed at 2500 rpm for 1 minute. The mixture was kept at least overnight before it was tested for pH and antimicrobial activity.

Example 3

Procedure: A mixture of the ingredients listed in Table 2 was prepared with a procedure similar to Example 1. The, CAP and the water were charged into cup 1 and mixed at 2500 rpm for 30 seconds. After this time, the sodium citrate and the citric acid were charged into cup 1 and mixed for an additional 30 seconds at 2500 rpm. In cup 2, the glycerol and the HHX were mixed at 2500 rpm for 30 seconds and subsequently transferred to cup 1. The resulting composition in cup 1 was mixed at 2500 rpm for 1 minute. The mixture was kept at least overnight before using for further testing.

Example 4

Procedure: A mixture of the ingredients listed in Table 2 was prepared with a procedure similar to Example 1. The BAC solution, the CAP and the water were charged into cup 1 and mixed at 2500 rpm for 30 seconds. After this time, the sodium citrate and the citric acid were charged into cup 1 and mixed for an additional 30 seconds at 2500 rpm. In cup 2, the glycerol and the HHX were mixed at 2500 rpm for 30 seconds and subsequently transferred to cup 1. The resulting composition in cup 1 was mixed at 2500 rpm for 1 minute. The mixture was kept at least overnight before using for further testing.

Example 5

Procedure: The water and crosslinked PVP K-90 mixture was made in overhead stirrer. In a 32 oz glass jar, 445 grams water was weighed and then kept under mechanical stirrer. 55 g of crosslinked K90 PVP was added at once and allowed to mix for 2 hours. After this time, the mixture was rolled overnight. The formulation with actives was prepared using a dual asymmetric centrifuge mixer using the components listed in Table 1. The BAC solution, the CAP, the glycerol, the PVP K-90/water mixture, the sodium citrate solution, and the citric acid solution were charged into a max 100 ml Flacktek cup and mixed at 2500 rpm for 60 seconds. The mixture was kept at least overnight before using for further testing.

Example 6

The PVP K-90/water mixture was made as described in Example 5. The formulation with actives was prepared using the dual asymmetric centrifuge mixer described in Example 1 and the components listed in Table 1. The BAC solution, the CAP, the glycerol, the PVP K-90/water mixture, the sodium citrate solution, and the citric acid solution were charged into a max 100 ml Flacktek cup and mixed at 2500 rpm for 60 seconds. The mixture was kept at least overnight before using for further testing.

Example 7

A mixture was prepared using a dual asymmetric centrifuge mixer (described above) and the components listed in Table 2. The BAC solution, the CAP and the water were charged into a max 100 ml Flacktek cup ("cup 1") and mixed at 2500 rpm for 30 seconds. After this time, the sodium citrate and the citric acid were charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 8

A mixture was prepared using a dual asymmetric centrifuge mixer (described above) and the components listed in Table 2. The BAC solution, the CAP and the water were charged into a max 100 ml Flacktek cup ("cup 1") and mixed at 2500 rpm for 30 seconds. After this time, the succinic acid and the NaOH solution were charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition in cup 1 was mixed at 2500 rpm for 1 minute. The mixture was kept at least overnight before using for further testing.

Example 9

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the citric acid and the NaOH solution were charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 10

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the gluconic acid solution and the NaOH solution were charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 11

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the lactic acid solution and the NaOH solution were charged into cup 1 and subsequently mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 12

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the tartaric acid and the NaOH solution were charged into cup 1 and subsequently mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 13

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the EDTA was charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 14

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the adipic acid and the NaOH solution were charged into cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 15

Procedure: A mixture was prepared using a dual asymmetric centrifuge mixer (described above) and the components listed in Table 3. The BAC solution, the CAP and the water were charged into a max 100 ml Flacktek cup ("cup 1") and mixed at 2500 rpm for 30 seconds. After this time, the gluconic acid and the NaOH solution were charged into the cup 1 and mixed for an additional 30 seconds at 2500 rpm. In a max 40 ml Flacktek cup ("cup 2"), the glycerol and the HHX were mixed at 2500 rpm for 30 seconds and subsequently transferred to cup 1. The resulting composition was mixed at 2500 rpm for 1 minute. The mixture was kept at least overnight before using for further testing.

Example 16

Procedure: The water and crosslinked PVP K-90 mixture was made as described in Example 5. The formulation with actives was prepared using a dual asymmetric centrifuge mixer (described above). The BAC solution, the CAP, the glycerol, the PVP K-90 solution, the succinic acid, and the NaOH solution were charged into a max 100 ml Flacktek cup and mixed at 2500 rpm for 60 seconds. The mixture was kept at least overnight before using for further testing.

All the compositions were subjected to the pH Test and Colony Biofilm Test as described herein. The results are shown in Table 5. Every composition of Examples 1-16 showed antimicrobial activity as evidenced by LRV's of at least 1.47. Most compositions had an LRV of >5.0 and many had an LRV of >7.0. In addition to the highly-effective antimicrobial properties, all compositions with a pH greater than 3 or greater than about 4 provide antimicrobial efficacy, as well as lower irritation to skin and wound tissue.

Comparative Example 1

Procedure: A mixture of the ingredients listed in Table 4 was prepared with a procedure similar to Example 1. The BAC solution, and the water were charged into cup 1 and mixed at 2500 rpm for 30 seconds. After this time, the sodium citrate and the citric acid were charged into cup 1 and mixed for an additional 30 seconds at 2500 rpm. In cup 2, the glycerol and the HHX were mixed at 2500 rpm for 30 seconds and subsequently transferred to cup 1. The resulting composition in cup 1 was mixed at 2500 rpm for 1 minute. The mixture was kept at least overnight before it was subsequently tested for pH and antimicrobial activity.

TABLE 4

Composition of Comparative Example 1. Values for each component are listed in grams (g).

| Component | Comparative Example 1 |
|---|---|
| Glycerol | 10 |
| Natrosol ™ 250 HHX | 3 |
| BAC (50% in water) | 0.1 |
| CAP | — |
| Water | 87.05 |
| Sodium Citrate | 0.2 |
| Citric acid Monohydrate | 0.15 |

TABLE 5

Results of pH Tests and Colony Biofilm Tests for Examples 1-16 and Comparative Example 1. The LRV was calculated as described in the Colony Biofilm Test.

| Sr. No. | pH | LRV | SD |
|---|---|---|---|
| Example 1 | 4.67 | 7.61 | 0.00 |
| Example 2 | 4.63 | 5.69 | 1.67 |
| Example 3 | 4.60 | 6.79 | 0.88 |
| Example 4 | 4.63 | 7.61 | 0.00 |
| Example 5 | 4.64 | 7.55 | 0.00 |
| Example 6 | 4.62 | 7.55 | 0.00 |
| Example 7 | 4.38 | 7.55 | 0.00 |
| Example 8 | 4.40 | 7.64 | 0.00 |
| Example 9 | 4.59 | 7.64 | 0.00 |
| Example 10 | 4.41 | 4.39 | 2.82 |
| Example 11 | 4.64 | 1.47 | 0.79 |
| Example 12 | 4.65 | 5.66 | 2.15 |

TABLE 5-continued

Results of pH Tests and Colony Biofilm Tests for Examples 1-16 and Comparative Example 1. The LRV was calculated as described in the Colony Biofilm Test.

| Sr. No. | pH | LRV | SD |
|---|---|---|---|
| Example 13 | 4.65 | 7.64 | 0.00 |
| Example 14 | 4.55 | 7.64 | 0.00 |
| Example 15 | 4.65 | 2.91 | 0.07 |
| Example 16 | 4.37 | 7.64 | 0.00 |
| Comparative Example 1 | 4.88 | 1.31 | 0.00 |

What is claimed is:

1. An antiseptic composition, comprising:
 a quaternary ammonium antiseptic component present in an amount of at least 0.04% by weight, the quaternary ammonium antiseptic component being a benzalkonium halide;
 a polycarboxylic acid chelator of one or more of citric acid and citrate present in a concentration of at least 0.05 M;
 a (C8-C12) 1,2 alkane diol; and
 water;
 wherein the antiseptic composition is characterized by a pH that is greater than or equal to 3.5 and less than 5.5 at 23° C.;
 wherein the water is present in the antiseptic composition at a greater weight percent than each of the quaternary ammonium antiseptic component, the polycarboxylic acid chelator, and the (C8-C12) 1,2-alkane diol.

2. The antiseptic composition of claim 1, wherein the quaternary ammonium antiseptic component is a benzalkonium chloride.

3. The antiseptic composition of claim 1, further comprising a betahydroxy acid.

4. The antiseptic composition of claim 3, wherein the betahydroxy acid is selected from the group consisting of betahydroxypropionic acid, salicylic acid, betahydroxybutanoic acid, tropic acid, and trethocanic acid.

5. The antiseptic composition of claim 1, wherein the quaternary ammonium antiseptic component is present in an amount of up to 1.0% by weight.

6. The antiseptic composition of claim 1, wherein the polycarboxylic acid chelator is present in an amount of 0.5% to 25% by weight.

7. The antiseptic composition of claim 1, wherein the (C8-C12) 1,2 alkane diol is present in an amount of 0.05% by weight to 3% by weight.

8. The antiseptic composition of claim 1, wherein the (C8-C12) 1,2 alkane diol is 1,2-octane diol.

9. The antiseptic composition of claim 1, characterized by a pH that is greater than or equal to 3.8 and less than 5.0 at 23° C.

10. The antiseptic composition of claim 1, further comprising an alphahydroxy acid.

11. The antiseptic composition of claim 10, wherein the alphahydroxy acid is selected from a group consisting of mandelic acid or a salt thereof, gluconic acid or a salt thereof, gluconolactone, glycolic acid or a salt thereof, lactic acid or a salt thereof, and a combination thereof.

12. The antiseptic composition of claim 10, wherein the alphahydroxy acid is present in an amount of up to 10% by weight.

13. A method of treating a wound, the method comprising applying the antiseptic composition of claim 1 to a wound site.

14. An antiseptic composition, comprising:
 a quaternary amine antiseptic component present in an amount of at least 0.04% by weight, the quaternary amine antiseptic component being a benzalkonium halide;
 a polycarboxylic acid chelator of one or more of citric acid and citrate present in a concentration of at least 0.05 M;
 a (C8-C12) 1,2 alkane diol; and
 water present in an amount from 0% to 75% by weight;
 wherein when the antiseptic composition is characterized by a pH that is greater than or equal to 3.5 and less than 5.5 at 23° C. when the antiseptic composition comprises <50% water by weight.

15. An antiseptic composition, comprising:
 a quaternary amine antiseptic component present in an amount of at least 0.04% by weight, the quaternary amine antiseptic component being a benzalkonium halide;
 a polycarboxylic acid chelator of one or more of citric acid and citrate present in a concentration of at least 0.05 M;
 a (C8-C12) 1,2 alkane diol; and
 water;
 wherein the antiseptic composition is characterized by a pH that is greater than or equal to 3.5 and less than 5.5 at 23° C.;
 wherein the water is present in the antiseptic composition at a greater weight percent than any other component of the antiseptic composition.

* * * * *